（12) United States Patent
Ryokawa et al.

(10) Patent No.: US 8,680,308 B2
(45) Date of Patent: Mar. 25, 2014

(54) HAFNIUM AMIDE COMPLEX MANUFACTURING METHOD AND HAFNIUM-CONTAINING OXIDE FILM

(75) Inventors: Atsushi Ryokawa, Ube (JP); Shuhei Yamada, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 216 days.

(21) Appl. No.: 13/129,490

(22) PCT Filed: Nov. 11, 2009

(86) PCT No.: PCT/JP2009/069157
§ 371 (c)(1),
(2), (4) Date: May 16, 2011

(87) PCT Pub. No.: WO2010/064524
PCT Pub. Date: Jun. 10, 2010

(65) Prior Publication Data
US 2011/0230671 A1 Sep. 22, 2011

(30) Foreign Application Priority Data

Dec. 2, 2008 (JP) ................................. 2008-307841

(51) Int. Cl.
*C07F 7/00* (2006.01)
(52) U.S. Cl.
USPC .......................................................... 556/51
(58) Field of Classification Search
USPC .......................................................... 556/51
See application file for complete search history.

(56) References Cited

U.S. PATENT DOCUMENTS

| 6,486,080 | B2 * | 11/2002 | Chooi et al. | 438/785 |
| 2005/0065358 | A1 | 3/2005 | Itsuki et al. | |
| 2005/0214458 | A1 * | 9/2005 | Meiere | 427/248.1 |
| 2007/0197809 | A1 | 8/2007 | Ryokawa et al. | |
| 2008/0081922 | A1 * | 4/2008 | Meiere et al. | 556/51 |
| 2009/0005584 | A1 | 1/2009 | Yamada et al. | |

FOREIGN PATENT DOCUMENTS

| JP | 2005-263771 A | 9/2005 |
| JP | 2005-298467 A | 10/2005 |
| JP | 2005-314785 A | 11/2005 |
| JP | 2007-051042 A | 3/2007 |
| JP | 2008-189550 A | 8/2008 |

OTHER PUBLICATIONS

Hausmann, D. et al. "Atomic layer deposition of hafnium and zirconium oxides using metal amide precursors," Chem. Mater. (2002) 14: 4350-4358.*
Teren, A. et al. "Comparison of precursors for pulsed metal-organic chemical vapor deposition of HfO2 high-K dielectric thin films," Thin Solid Films (2005) 478: 206-217.*
Yang, T. et al. "Chemical vapor deposition of HfO2 thin films using the novel single precursor hafnium 3-methyl-3-pentoxide, Hf(mp)4," Chem. Mater. (2005) 17: 6713-6718.*
Korean Office Action dated Nov. 9, 2012 (3 pages).
D.C. Bradley, et al., "Metallo-organic Compounds Containing Metal-Nitrogen Bonds. Part VI. Infrared and Nuclear Magnetic Resonance of Dialkylamido-derivatives of Titanium, Vanadium, Zirconium, Niobium, Hafnium, Tantalum, and Thorium", J. Chem. Soc., (A), 1969, p. 980-984.
Lecture Previous Texts for 54$^{th}$ Applied Physics-related Association Lecture, 2007, p. 18, vol. 0.
International Search Report including English translation dated Dec. 8, 2009 and PCT/ISA/237 Form (Nine (9) pages).

* cited by examiner

*Primary Examiner* — Porfirio Nazario Gonzalez
(74) *Attorney, Agent, or Firm* — Crowell & Moring LLP

(57) ABSTRACT

Disclosed is a method of producing a hafnium amide complex represented by general formula: $Hf(NR_4R_5)_4$, characterized by comprising: carrying out a reduced-pressure distillation after a lithium alkylamide represented by general formula: $Li(NR_4R_5)$ is added to and allowed to react with a tertiary hafnium alkoxide complex represented by general formula: $Hf[O(CR_1R_2R_3)]_4$. (In the formulas, $R_1$, $R_2$ and $R_3$ independently represent either a phenyl group, a benzyl group, or a primary, secondary or tertiary alkyl group having a carbon number 1-6; and $R_4$ and $R_5$ independently represent either a methyl group or an ethyl group; however, a case where all of $R_1$, $R_2$ and $R_3$ are methyl groups, and a case where one of $R_1$, $R_2$ and $R_3$ is an ethyl group and the other two are methyl groups are excluded.)

1 Claim, 1 Drawing Sheet

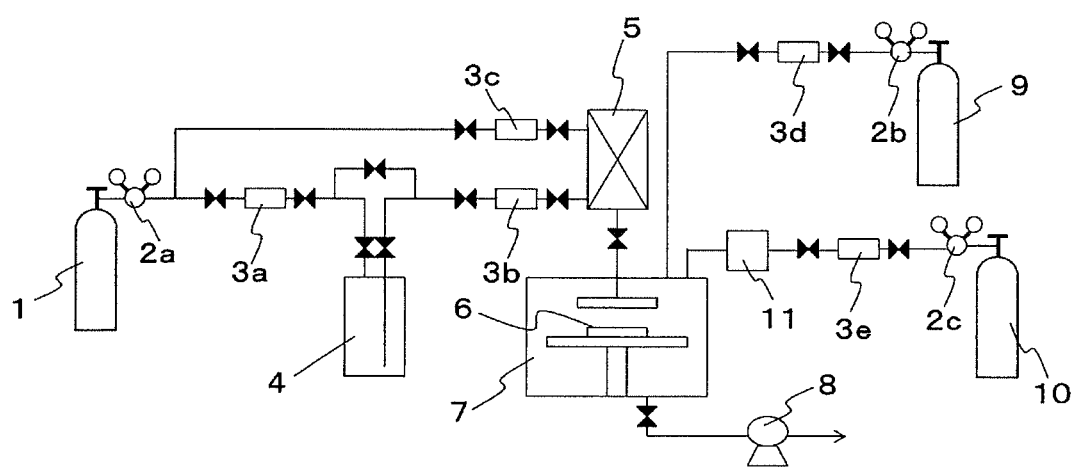

HAFNIUM AMIDE COMPLEX MANUFACTURING METHOD AND HAFNIUM-CONTAINING OXIDE FILM

TECHNICAL FIELD

This invention relates to a production method of a hafnium amide complex on which a hopeful view is taken as a hafnium-film formation raw material for a hafnium-containing oxide film ($HfO_2$, $Hf_xSi_yO_z$, $Hf_xAl_yO_z$ or the like) on which attention is paid as a following generation high dielectric constant gate oxide film in semiconductor production, and to a hafnium-containing oxide film produced by using this production method.

BACKGROUND OF INVENTION

Hitherto $SiO_2$ has been continued to be used for a gate oxide film in semiconductor production for many years. The reason for this is that speeding-up of the operating speed of an element with upgraded integration of semiconductor could be dealt with by promoting film-thinning of $SiO_2$. However, in these years, as a result of the fact that speeding-up of the operation speed of the element is further promoted in order to attain upgrading of functionality and integration of LSI, a physical limit for film-thinning of $SiO_2$ has come near and therefore it has become difficult to deal with further speeding-up. In view of this, attention has been paid on a hafnium-containing oxide film as a gate oxide film in place of $SiO_2$. The hafnium-containing oxide film is high severalhold in dielectric constant as compared with $SiO_2$, and therefore it becomes possible to increase a physical film thickness corresponding to speeding-up of operational speed of the element as compared with that of $SiO_2$.

As film formation process for this hafnium-containing oxide film, there are two kinds, a physical vapor-phase growth process (Physical Vapor Deposition, abbreviated hereinafter as PVD) and a chemical vapor-phase growth process (Chemical Vapor Deposition, abbreviated hereinafter as CVD). In general, with PVD process, forming a uniform film on a substrate having unevenness is difficult, and controlling a film composition is difficult. In contrast, with CVD process, formation of a uniform film on a substrate is possible regardless of presence or absence of unevenness, and controllability for a film composition is also excellent. In film formation of the gate oxide film, there is a case that formation of a uniform film on a part having unevenness is required, according to process of gate stack production. Additionally, it becomes important to control the film composition because the film composition affects the electrical properties of semiconductor. Therefore, it has become a main stream to use CVD process as a film formation process for the gate oxide film.

In order to carry out the film formation of a hafnium-containing oxide film by CVD process, a hafnium film formation raw material high in vapor pressure is required, in which hafnium amide complex is relatively high in volatility and expanding in use as a film formation raw material for the hafnium-containing oxide film as a semiconductor gate oxide film by CVD process. As a production process for the hafnium amide complex, a process for allowing hafnium tetrachloride ($HfCl_4$) and lithium alkylamide to react each other in an organic solvent is general.

For example, a process for allowing hafnium tetrachloride ($HfCl_4$) and lithium diethylamide [$LiN(CH_2CH_3)_2$] to react each other in a hexane solvent to synthesize tetrakis(diethylamido)hafnium $\{Hf[N(CH_2CH_3)_2]_4\}$ is disclosed (see Non-patent Citation 1).

The gate oxide film is required to be a film having an extremely high purity because of being positioned at a lowermost layer section of semiconductor, and therefore the hafnium amide complex as the film formation raw material therefor is also required to be a high purity product. A zirconium component originated from a raw material, of impurities contained in the hafnium amide complex is contained usually at a high concentration of about 1000 to 5000 mass ppm. This is because hafnium and zirconium are the same group elements and have similar chemical properties under lanthanoid contraction so as to be very difficult to be separated from each other.

It is pointed out that a zirconium oxide is low in heat resistance as compared with a hafnium oxide, and the zirconium oxide is taken into a film depending upon a zirconium impurity concentration in a hafnium film formation raw material, thereby raising contingent trouble of a device. Thus, it is required to lower a zirconium concentration in the film. Accordingly, using a hafnium film formation raw material lowered in zirconium concentration is important for ensuring a reliability of the device (see Non-patent Citation 2).

As production method for a hafnium film formation raw material lowered in zirconium concentration, there are a production method for hafnium amide complex by a reduced-pressure rectification (see Patent Citation 1 and Patent Citation 2), a method of production by light irradiation or by passing through a chelate-carrying column (see Patent Citation 3), a method of producing a hafnium film formation raw material after carrying out a recrystallization for hafnium halide with an organic solvent having ether linkage (see Patent Citation 4), a production method for hafnium amide complex by carrying out a reduced-pressure distillation after additive such as $CF_3SO_3H$ or the like is added to hafnium amide complex (see Patent Citation 5), and the like. For example, Japanese Patent Provisional Publication No. 2005-298467 (Patent Citation 2) describes a method of separating zirconium component in tetrakis(dimethylamido)hafnium by a reduced-pressure rectification, in which ligand of hafnium amide complex is limited to tetrakis(dimethylamido)hafnium having dimethylamino group so that application cannot be made to hafnium amide complex such as tetrakis(ethylmethylamido)hafnium or tetrakis(diethylamido)hafnium.

Additionally, in Japanese Patent Provisional Publication No. 2005-314785 (Patent Citation 3) and Japanese Patent Provisional Publication No. 2007-051042 (Patent Citation 4), there is no description of yield and yield point of hafnium amide complex so that it is not apparent as to whether execution is economically possible or not.

PRIOR ART CITATIONS

Patent Citation

Patent Citation 1: Japanese Patent Provisional Publication No. 2005-263771

Patent Citation 2: Japanese Patent Provisional Publication No. 2005-298467

Patent Citation 3: Japanese Patent Provisional Publication No. 2005-314785

Patent Citation 4: Japanese Patent Provisional Publication No. 2007-051042

Patent Citation 5: Japanese Patent Provisional Publication No. 2008-189550

Non-Patent Citation

Non-Patent Citation 1: J. Chem. Soc. (A), 980 (1969)
Non-Patent Citation 2: Lecture Previous Texts for 54th Applied Physics-related Association Lecture, Volume 0, page 18 (2007)

SUMMARY OF THE INVENTION

An object of the present invention is to provide a method of producing a hafnium amide complex suitable as a semiconductor film formation material capable of providing a hafnium-containing oxide film, at a high yield and easily.

In order to attain the above object, the present inventors have repeatedly made many eager studies. As a result, they have found a method of producing a hafnium amide complex at a high yield and easily by carrying out a reduced-pressure distillation operation after a lithium alkylamide is added to and allowed to react with a tertiary hafnium alkoxide complex, and have reached the present invention.

In other words, the present invention is to provide a method of producing a hafnium amide complex represented by general formula: $Hf(NR_4R_5)_4$, characterized by comprising: carrying out a reduced-pressure distillation after a lithium alkylamide represented by general formula: $Li(NR_4R_5)$ is added to and allowed to react with a tertiary hafnium alkoxide complex represented by general formula: $Hf[O(CR_1R_2R_3)]_4$ (in the formulas, $R_1$, $R_2$ and $R_3$ independently represent either a phenyl group, a benzyl group, or a primary, secondary or tertiary alkyl group having a carbon number 1-6; and R4 and R5 independently represent either a methyl group or an ethyl group; however, a case where all of $R_1$, $R_2$ and $R_3$ are methyl groups, and a case where one of $R_1$, $R_2$ and $R_3$ is an ethyl group and the other two are methyl groups are excluded.).

Further, the present invention is to provide a hafnium-containing oxide film produced by a chemical vapor-phase growth process, using the hafnium amide complex produced by the above-mentioned production method as a hafnium source.

BRIEF DESCRIPTION OF DRAWINGS

FIG. 1 is a schematic illustration showing a configuration of a CVD apparatus used in Examples of the present invention.

DETAILED DESCRIPTION

According to a production method of the present invention, a hafnium amide complex can be produced at a high yield and easily. Additionally, the present invention can provide a hafnium-containing oxide film lowered in zirconium concentration in a film.

Hereinafter, the present invention will be discussed further in detail.

This invention is applied to a hafnium amide complex to be employed for a use requiring a high impurity, such as a semiconductor production process or the like. The hafnium amide complex in the present invention is used for, for example, a CVD material or the like for a high dielectric constant gate oxide film formation in a semiconductor production process, and is a hafnium amide complex represented by a general formula: $Hf(NR_4R_5)_4$ (in the formula, $R_4$ and $R_5$ independently represent either a methyl group or an ethyl group).

The present invention is carried out such that a lithium alkylamide is added to a tertiary hafnium alkoxide complex thereby to convert the tertiary hafnium alkoxide complex to a hafnium amide complex and the lithium alkylamide to a lithium alkoxide, and thereafter the hafnium amide complex is isolated by a reduced-pressure distillation.

Additionally, a zirconium concentration in the hafnium amide complex produced by the present invention can be made from a zirconium mole concentration of the tertiary hafnium alkoxide complex as a raw material without concentration in a production process. For example, in case that tetrakis(ethylmethylamido)hafnium $\{Hf[N(CH_3)(CH_2CH_3)]_4\}$, (molecular weight: 411) is produced according to the present method by using a raw material of tetra(2-methyl-2-pentanoxy)hafnium $\{Hf[OC(CH_3)_2(CH_2CH_2CH_3)]_4\}$, (molecular weight: 583) having a zirconium concentration of 638 mol ppm (100 mass ppm) as the tertiary hafnium alkoxide complex, the hafnium amide complex whose zirconium concentration corresponds to about 638 mol ppm (141 mass ppm) can be obtained. Here, conversion of mass concentration of zirconium to mol concentration of zirconium is made according to the following Equation 1:

$$\text{zirconium mol concentration} = \text{zirconium mass concentration} \times (\text{molecular weight of hafnium component/atomic weight of zirconium})  \quad \text{Equation 1}$$

In case that film formation is made using the hafnium amide complex high in zirconium concentration, the concentration of zirconium taken in a film become high thereby affecting reliability of a device, so that the zirconium concentration in the film is desirably controlled to be not higher than 300 mass ppm, more preferably not higher than 30 mass ppm, and further preferably not higher than 3 mass ppm. For this purpose, the zirconium concentration in the hafnium amide complex as the material for semiconductor film formation is desirably made to be not higher than 100 mass ppm, more preferably not higher than 10 mass ppm, and further preferably not higher than 1 mass ppm.

As the hafnium alkoxide complex, a tertiary hafnium alkoxide complex high in steric hindrance of ligand and forming a monomer is used.

In case of using a primary hafnium alkoxide complex such as tetraethoxy hafnium $[Hf(OCH_2CH_3)_4]$ or a secondary hafnium alkoxide complex such as tetraisopropoxy hafnium $\{Hf[OCH(CH_3)_2]_4\}$, steric hindrance of ligand is low and therefore the hafnium alkoxide complex forms a polymer, so that reaction does not sufficiently proceed.

Additionally, it is preferable to use a tertiary hafnium alkoxide represented by a general formula: $Hf[O(CR_1R_2R_3)]_4$ whose ligands $R_1$, $R_2$ and $R_3$ independently represent either a phenyl group, a benzyl group, or a primary, secondary or tertiary alkyl group having a carbon number 1-6, excluding a case where all of $R_1$, $R_2$ and $R_3$ are methyl groups and a case where one of $R_1$, $R_2$ and $R_3$ is an ethyl group and the other two are methyl groups.

In case of using tetra-tertiary-butoxy hafnium $\{Hf[OC(CH_3)_3]_4\}$ in which all of $R_1$, $R_2$ and $R_3$ are methyl groups, by-produced lithium tertiary butoxide has a sublimation point of 90° C./0.13 kPa, and in case of using tetra(2-methyl-2-butoxy)hafnium $\{Hf[OC(CH_3)_2(CH_2CH_3)]_4\}$ in which one of $R_1$, $R_2$ and $R_3$ is an ethyl group and the other two are methyl groups, by-produced lithium tertiary amyl oxide has a sublimation point of 110° C./0.13 kPa. Thus, since a molecular weight in either case is low, the by-produced lithium alkoxide has a low sublimation point, so that a vapor pressure difference between the objective hafnium amide complex and lithium alkoxide as a by-product becomes small. As a result, the lithium alkoxide as the by-product is unavoidably mixed into the fraction of the hafnium amide complex during execution of the reduced-pressure distillation, which is not preferable.

Additionally, concerning tertiary hafnium alkoxide complexes represented by general formulas other than the above-mentioned general formula $Hf[O(CR_1R_2R_3)]_4$, ligand is not general so as to be economically not preferable.

Concrete examples represented as the tertiary hafnium alkoxide complex include Compounds No. 1 to No. 12 shown below.

[Chem.1]

Compound No. 1

Compound No. 2

Compound No. 3

Compound No. 4

Compound No. 5

Compound No. 6

Compound No. 7

Compound No. 8

Compound No. 9

Compound No. 10

Compound No. 11

Compound No. 12

Of these, Compound No. 11 or Compound No. 12 which are inexpensively available tertiary hafnium alkoxide complexes and whose alcohol body as ligand is used as an aroma chemical are preferable.

Production of the tertiary hafnium alkoxide complex is not particularly limited, and therefore known methods can be used for the production, in which it is preferable to use the tertiary hafnium alkoxide complex low in zirconium concentration as discussed above. For example, the tertiary hafnium alkoxide complex low in zirconium concentration can be obtained by using a method described in Japanese Patent Application No. 2008-131124 which is an unpublished earlier application at the time of filing of the present application.

The lithium alkylamide to be used is one having the same substituent as amide ligand of the hafnium amide complex which is an objective product. In other words, in case of producing tetrakis(diethylamido)hafnium, lithium diethylamide is used as the lithium alkylamide; and in case of producing tetrakis(dimethylamido)hafnium, lithium dimethylamide is used as the lithium alkylamide.

A used amount of the lithium alkylamide is preferably 1 to 10 equivalent relative to 1 equivalent of the tertiary hafnium alkoxide complex represented by the general formula: $Hf[O(CR_1R_2R_3)]_4$. If less than 1 equivalent, there is a fear that the tertiary hafnium alkoxide complex unavoidably remains thereby lowering a yield; and even if more than 10 equivalent is used, improvement in yield cannot be expected and therefore not economical.

The lithium alkylamide is powdery and solid at ordinary temperature, in which it may be added in the form of solid into the tertiary hafnium alkoxide complex represented by the above-mentioned general formula: $Hf[O(CR_1R_2R_3)]_4$ or may be added in the state of being dissolved in an organic solvent such as ether or the like, into the tertiary hafnium alkoxide complex.

A temperature at which the lithium alkylamide is added into the tertiary hafnium alkoxide complex represented by the above-mentioned general formula: $Hf[O(CR_1R_2R_3)]_4$ is preferably within a range of from −78 to 200° C., more preferably a range of from 0° C. to 100° C. If added at a temperature higher than 200° C., there is a fear that the lithium alkylamide may make its autolysis under the action of heat.

From the viewpoint of uniformizing a reaction liquid, after the lithium alkylamide is added, it is preferable to carry out a reduced-pressure distillation after agitation is made for 1 to 3 hours by an agitator or the like.

The reduce-pressure distillation is carried out according to a conventional manner, in which a temperature range is preferably from 80 to 150° C., and a pressure range is preferably from 0.05 to 0.5 kPa. If the reduced-pressure distillation is carried out at a temperature higher than 150° C., there is a fear that the by-produced lithium alkoxide vaporizes or sublimes and is mixed into the hafnium amide complex as a fraction; and if it is carried out at a temperature lower than 80° C., vaporization of the hafnium amide complex retards so as not to be effective. If it is carried out at a pressure higher than 0.5 kPa, the hafnium amide complex does not sufficiently vaporize so as not to be effective; and if is carried out at a temperature lower than 0.05 kPa, a reduced-pressure distillation equipment is not economical.

By accomplishing isolation under the reduced-pressure distillation, the hafnium amide complex whose by-produced lithium alkoxide component is not higher than 100 mass ppm can be obtained.

A hafnium-containing oxide film according to the present invention can be obtained by a CVD process in which a raw material gas containing the hafnium amide complex obtained according to the present invention is heated as a hafnium source for constituting a film; and vapor generated upon vaporization of the raw material gas is introduced into a reaction chamber so that the vaporized hafnium amide complex is decomposed or undergoes reaction, thereby growing and depositing the hafnium-containing oxide film on a substrate. As method of forming the hafnium-containing oxide film by the CVD process, many processes described in known literatures can be applied, in which a deposition process, a transporting process for the raw material, a film formation condition and the like are not particularly limited, and therefore formation of the hafnium-containing oxide film can be carried out under conditions and manners of usual processes.

In case of using a raw material gas other than the hafnium amide complex as occasion demands, a multinary hafnium-containing oxide film can be obtained. For example, in case of using a silicon-based raw material gas, a ternary HfxSiyOz film or the like is obtained. In case of using an aluminum-based raw material gas, a ternary HfxAlyOz film or the like is obtained. Examples of the above-mentioned silicon-based raw material gas include tetraethoxysilane [Si(OCH$_2$CH$_3$)$_4$], tris(dimethylamino)silane {HSi[N(CH$_3$)$_2$]$_3$}, tetrakis(dimethylamino)silane {Si[N(CH$_3$)$_2$]$_4$} and the like.

An example of the aluminum-based raw material is trimethylaluminium [Al(CH$_3$)$_3$]. The raw material gas other than the hafnium amide complex to be used as occasion demands may be supplied to one raw material tank or independently to each raw material tank, in which supplying independently to each raw material tank is preferable in order to precisely control a thin film composition. A used amount of the raw material gas other than the hafnium amide complex is suitably selected according to an objective thin film composition in any case.

Additionally, examples of reactive gas to be used as occasion demands include ones set forth below. Examples of oxidizing one include oxygen, ozone, water vapor, hydrogen peroxide, nitrogen monoxide, nitrogen dioxide, and the like. An example of reducing one includes hydrogen. Examples of one producing a nitride-containing film include organic amine compound such as monoalkylamine, dialkylamine, trialkylamine and the like, ammonia, hydrazine, and the like.

Additionally, examples of the CVD process to be used in the present invention include a thermal CVD process for depositing the raw material gas and the reactive gas as an oxide film under heating, a plasma CVD process for depositing an oxide film under heat or plasma, an ALCVD (Atomic Layer Chemical Vapor Deposition) process in which each atom layer is piled one upon another one by one by repeatedly carrying out a cycle including adsorption of molecule of the raw material gas onto a surface as each monolayer, film formation upon reaction with the reactive gas, and removal of excessive molecule by purging, and the like.

Additionally, examples of the transporting process for the raw material include a gas transporting process for vaporizing the hafnium amide complex under heating or pressure reduction and introducing the complex together with a carrier gas such as argon, nitrogen, helium or the like used as occasion demands into a reaction chamber, a liquid transporting process for introducing the hafnium amide complex in the state of liquid or solution into a vaporizing chamber and vaporizing the complex under heating or pressure reduction so as to introduce the complex into a reaction chamber, and the like.

Additionally, examples of the film formation condition includes temperature, pressure, deposition rate and the like. Concerning the temperature, a temperature on a substrate is recommended to be within a range of from 100 to 800° C., preferably a range of from 150° C. to 500° C., in order to make sufficient reaction of the hafnium amide complex as the raw material gas. The pressure is preferably within a range of from 10 Pa to 100 kPa in case of the thermal CVD, and is preferably within a range of from 10 to 50 Pa in case of the plasma CVD. The deposition rate can be controlled by supplying condition (vaporizing temperature and vaporizing pressure) for the raw material, reaction temperature and reaction pressure. Concerning the deposition rate, if it is too high, multilevel covering characteristics and the like of the film are degraded; and if it is to low, productivity is degraded so as not to be economically preferable. Therefore, deposition is recommended to be made at a deposition rate of from 0.01 to 100 nm/second, preferably from 0.02 to 20 nm/second. Additionally, in case of the ALCVD process, number of the above-mentioned cycle may be controlled to obtain a desired film thickness.

Additionally, after deposition of a thin film, an annealing treatment under heating may be carried out in order to obtain better electric characteristics. The annealing treatment is recommended to be made at a heating temperature or temperature on a substrate, within a range of from 400 to 1200° C., preferably 500° C. to 800° C.

Hereafter, the present invention will be discussed in detail with reference to Examples; however, the present invention is not limited to Examples set forth below.

EXAMPLES

Synthesis of Tertiary Hafnium Alkoxide Complex (1) Synthesis of Compound No. 1 Shown Below

[Chem. 2]

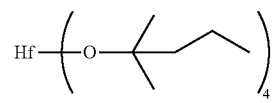

Compound No. 1

A 3 L five-neck glass flask was provided with a dropping funnel, a reflux condenser, a thermometer and an agitator, and nitrogen substitution was made for the inside of the flask. This flask was charged with 1000 g (2140 mmol) of tetrakis(diethylamido)hafnium {Hf[N(CH$_2$CH$_3$)$_2$]$_4$} whose zirconium concentration was 900 mass ppm, and cooled to 0° C. Thereafter, 35 g (230 mmol) of trifluoromethanesulfonic acid (CF$_3$SO$_3$H) was dropped from the dropping funnel over 1 hour. After termination of dropping, temperature-up was made to 20° C. while agitation was made for 1 hour. This reaction liquid underwent distillation under the condition of 125° C. and 0.12 kPa thereby obtaining 958 g of a fraction. The obtained fraction had tetrakis(diethylamido)hafnium {Hf[N(CH$_2$CH$_3$)$_2$]$_4$} as a major component according to ¹HNMR, and a zirconium concentration in the fraction was measured by an ICP spectrometry apparatus and was 492 mass ppm. Additionally, a trifluoromethanesulfonic acid ion concentration in the fraction was measured by an ion chromatography and was 1.6 mass %.

Next, a 3 L five-neck glass flask provided with a dropping funnel, a reflux condenser, a thermometer and an agitator was charged with 900 g of the obtained fraction, and was cooled to 0° C. Thereafter, 31 g (210 mmol) of trifluoromethanesulfonic acid ($CF_3SO_3H$) was dropped from the dropping funnel over 1 hour. After termination of dropping, temperature-up was made to 20° C. while agitation was made for 1 hour. This reaction liquid underwent distillation under the condition of 125° C. and 0.12 kPa thereby obtaining 839 g of a fraction. The obtained fraction had tetrakis(diethylamido) hafnium $\{Hf[N(CH_2CH_3)_2]_4\}$ as a major component according to ¹HNMR, and a zirconium concentration in the fraction was measured by an ICP spectrometry apparatus and was 163 mass ppm. Additionally, a trifluoromethanesulfonic acid ion concentration in the fraction was measured by an ion chromatography and was 1.7 mass %.

Next, a 3 L five-neck glass flask provided with a dropping funnel, a reflux condenser, a thermometer and an agitator was charged with 800 g of the obtained fraction, and was cooled to 0° C. Thereafter, 28 g (190 mmol) of trifluoromethanesulfonic acid ($CF_3SO_3H$) was dropped from the dropping funnel over 1 hour. After termination of dropping, temperature-up was made to 20° C. while agitation was made for 1 hour. This reaction liquid underwent distillation under the condition of 125° C. and 0.12 kPa thereby obtaining 714 g of a fraction. The obtained fraction had tetrakis(diethylamido) hafnium $\{Hf[N(CH_2CH_3)_2]_4\}$ as a major component according to ¹HNMR, and a zirconium concentration in the fraction was measured by an ICP spectrometry apparatus and was 48 mass ppm. Additionally, a trifluoromethanesulfonic acid ion concentration in the fraction was measured by an ion chromatography and was 1.4 mass %.

Next, a 3 L five-neck glass flask provided with a dropping funnel, a reflux condenser, a thermometer and an agitator was charged with 650 g of the obtained fraction, and was cooled to 0° C. Thereafter, 23 g (150 mmol) of trifluoromethanesulfonic acid ($CF_3SO_3H$) was dropped from the dropping funnel over 1 hour. After termination of dropping, temperature-up was made to 20° C. while agitation was made for 1 hour. This reaction liquid underwent distillation under the condition of 125° C. and 0.12 kPa thereby obtaining 602 g of a fraction. The obtained fraction had tetrakis(diethylamido) hafnium $\{Hf[N(CH_2CH_3)_2]_4\}$ as a major component according to ¹HNMR, and a zirconium concentration in the fraction was measured by an ICP spectrometry apparatus and was 20 mass ppm. Additionally, a trifluoromethanesulfonic acid ion concentration in the fraction was measured by an ion chromatography and was 1.5 mass %.

Next, a 3 L five-neck glass flask provided with a dropping funnel, a reflux condenser, a thermometer and an agitator was charged with 650 g of the obtained fraction, and was cooled to 0° C. Thereafter, 20 g (130 mmol) of trifluoromethanesulfonic acid ($CF_3SO_3H$) was dropped from the dropping funnel over 1 hour. After termination of dropping, temperature-up was made to 20° C. while agitation was made for 1 hour. This reaction liquid underwent distillation under the condition of 125° C. and 0.12 kPa thereby obtaining 497 g of a fraction. The obtained fraction had tetrakis(diethylamido) hafnium $\{Hf[N(CH_2CH_3)_2]_4\}$ as a major component according to ¹HNMR, and a zirconium concentration in the fraction was measured by an ICP spectrometry apparatus and was 6 mass ppm. Additionally, a trifluoromethanesulfonic acid ion concentration in the fraction was measured by an ion chromatography and was 1.6 mass %.

Next, a 1 L five-neck glass flask provided with a dropping funnel, a reflux condenser, a thermometer and an agitator was charged with 450 g of the obtained fraction, and was cooled to 0° C. Thereafter, 16 g (110 mmol) of trifluoromethanesulfonic acid ($CF_3SO_3H$) was dropped from the dropping funnel over 1 hour. After termination of dropping, temperature-up was made to 20° C. while agitation was made for 1 hour. This reaction liquid underwent distillation under the condition of 125° C. and 0.12 kPa thereby obtaining 405 g of a fraction. The obtained fraction had tetrakis(diethylamido) hafnium $\{Hf[N(CH_2CH_3)_2]_4\}$ as a major component according to ¹HNMR, and a zirconium concentration in the fraction was measured by an ICP spectrometry apparatus and was 2 mass ppm. Additionally, a trifluoromethanesulfonic acid ion concentration in the fraction was measured by an ion chromatography and was 1.6 mass %.

Next, a 1 L five-neck glass flask provided with a dropping funnel, a reflux condenser, a thermometer and an agitator was charged with 350 g of the obtained fraction, and was cooled to 0° C. Thereafter, 12 g (80 mmol) of trifluoromethanesulfonic acid ($CF_3SO_3H$) was dropped from the dropping funnel over 1 hour. After termination of dropping, temperature-up was made to 20° C. while agitation was made for 1 hour. This reaction liquid underwent distillation under the condition of 125° C. and 0.12 kPa thereby obtaining 311 g of a fraction. The obtained fraction had tetrakis(diethylamido)hafnium $\{Hf[N(CH_2CH_3)_2]_4\}$ as a major component according to ¹HNMR, and a zirconium concentration in the fraction was measured by an ICP spectrometry apparatus and was 0.8 mass ppm. Additionally, a trifluoromethanesulfonic acid ion concentration in the fraction was measured by an ion chromatography and was 1.5 mass %.

Next, a 1 L five-neck glass flask provided with a reflux condenser, a thermometer and an agitator was charged with 250 g of the obtained fraction, and 10 g (130 mmol) of lithium diethylamide $[LiN(C_2H_5)_2]$ was added into this flask, followed by agitation at room temperature for 1 hour. Subsequently, this reaction liquid underwent distillation under the condition of 125° C. and 0.12 kPa thereby obtaining 245 g of a fraction. The obtained fraction was tetrakis(diethylamido) hafnium $\{Hf[N(CH_2CH_3)_2]_4\}$ according to ¹HNMR, and a zirconium concentration in the fraction was 0.7 mass ppm. A trifluoromethanesulfonic acid ion concentration in the fraction was not more than 10 mass ppm.

It is to be noted that a yield from the charged tetrakis (diethylamido)hafnium $\{Hf[N(CH_2CH_3)_2]_4\}$ (zirconium concentration: 900 mass ppm) was 52 mass %.

A 100 mL five-neck glass flask provided with a dropping funnel, a reflux condenser, a thermometer and an agitator was charged with 20.0 g (42.8 mmol) of the obtained tetrakis (diethylamido)hafnium $\{Hf[N(CH_2CH_3)_2]_4\}$ whose zirconium concentration was 0.7 mass ppm, and cooled to 0° C. Thereafter, 19.2 g (188 mmol) of 2-methyl-2-pentanol was dropped from the dropping funnel over 1 hour. After termination of dropping, temperature-up was made to 20° C. while agitation was made for 1 hour. Subsequently, this reaction liquid underwent distillation under the condition of 50° C. and 0.12 kPa to distill out by-produced diethylamine and excessive alcohol content thereby obtaining 24.4 g of a liquid content. The obtained liquid content was the above-mentioned Compound No. 1 as a tertiary hafnium alkoxide complex according to ¹HNMR, and a zirconium concentration in the liquid was 0.6 mass ppm (yield: 98%).

(2) Synthesis of Compound No. 3 Shown Below.

[Chem. 3]

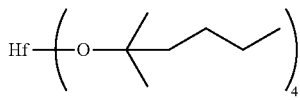

Compound No. 3

A liquid content in an amount of 27.3 g was obtained in the same process as in the synthesis of the above-mentioned (1) except for using 21.8 g (188 mmol) of 2-methyl-2-hexanol in place of 19.2 g (188 mmol) of 2-methyl-2-pentanol. The obtained liquid content was the above-mentioned Compound No. 3 as a tertiary hafnium alkoxide complex according to $^1$HNMR, and a zirconium concentration in the liquid was 0.5 mass ppm (yield: 100%).

(3) Synthesis of Compound No. 8 Shown Below

[Chem. 4]

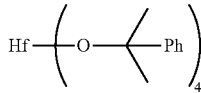

Compound No. 8

A liquid content in an amount of 30.8 g was obtained in the same process as in the synthesis of the above-mentioned (1) except for using 25.6 g (188 mmol) of 2-phenyl-2-propanol in place of 19.2 g (188 mmol) of 2-methyl-2-pentanol. The obtained liquid content was the above-mentioned Compound No. 8 as a tertiary hafnium alkoxide complex according to $^1$HNMR, and a zirconium concentration in the liquid was 0.5 mass ppm (yield: 100%).

(4) Synthesis of Compound 11 Shown Below

[Chem. 5]

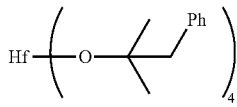

Compound No. 11

A liquid content in an amount of 33.2 g was obtained in the same process as in the synthesis of the above-mentioned (1) except for using 28.2 g (188 mmol) of dimethyl benzyl carbinol in place of 19.2 g (188 mmol) of 2-methyl-2-pentanol. The obtained liquid content was the above-mentioned Compound No. 11 as a tertiary hafnium alkoxide complex according to $^1$HNMR, and a zirconium concentration in the liquid was 0.4 mass ppm (yield: 100%).

(5) Synthesis of Compound No. 12 Shown Below

[Chem. 6]

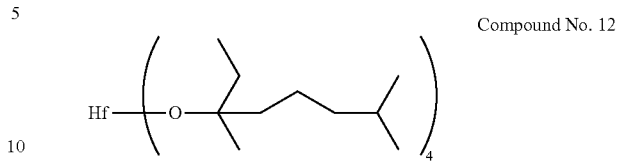

Compound No. 12

A liquid content in an amount of 34.2 g was obtained in the same process as in the synthesis of the above-mentioned (1) except for using 29.5 g (188 mmol) of 3,7-dimethyl-3-octanol in place of 19.2 g (188 mmol) of 2-methyl-2-pentanol. The obtained liquid content was the above-mentioned Compound No. 12 as a tertiary hafnium alkoxide complex according to $^1$HNMR, and a zirconium concentration in the liquid was 0.4 mass ppm (yield: 99%).

Example 1

A 100 mL five-neck glass flask provided with a dropping funnel, a reflux condenser, a thermometer and an agitator was charged with 20.0 g (34.3 mmol) of the above-mentioned Compound No. 1 which was obtained by the synthesis of the above-mentioned (1) as a tertiary hafnium alkoxide complex and had a zirconium concentration of 0.6 mass ppm. 7.7 g (151 mmol) of lithium dimethylamide [LiN(CH$_3$)$_2$] was added into this flask, followed by agitation at room temperature for 1 hour. Subsequently, this reaction liquid underwent distillation under the condition of 90° C. and 0.12 kPa thereby obtaining 9.2 g of a fraction. The obtained fraction was tetrakis(dimethylamido)hafnium {Hf[N(CH$_3$)$_2$]$_4$} according to $^1$HNMR, and a zirconium concentration in the fraction was 0.9 mass ppm. A 2-methyl-2-pentanoxy lithium concentration in the fraction was not more than 100 mass ppm (yield: 76%).

Example 2

A 100 mL five-neck glass flask provided with a dropping funnel, a reflux condenser, a thermometer and an agitator was charged with 20.0 g (31.3 mmol) of the above-mentioned Compound No. 3 which was obtained by the synthesis of the above-mentioned (2) as a tertiary hafnium alkoxide complex and had a zirconium concentration of 0.5 mass ppm. 8.1 g (125 mmol) of lithium ethylmethylamide [LiN(CH$_3$)(CH$_2$CH$_3$)] was added into this flask, followed by agitation at room temperature for 1 hour. Subsequently, this reaction liquid underwent distillation under the condition of 100° C. and 0.12 kPa thereby obtaining 10.3 g of a fraction. The obtained fraction was tetrakis(ethylmethylamido)hafnium {Hf[N(CH$_3$)(CH$_2$CH$_3$)]$_4$} according to $^1$HNMR, and a zirconium concentration in the fraction was 0.8 mass ppm. A 2-methyl-2-hexanoxy lithium concentration in the fraction was not more than 100 mass ppm (yield: 80%).

Example 3

A 100 mL five-neck glass flask provided with a dropping funnel, a reflux condenser, a thermometer and an agitator was charged with 20.0 g (27.8 mmol) of the above-mentioned Compound No. 8 which was obtained by the synthesis of the above-mentioned (3) as a tertiary hafnium alkoxide complex and had a zirconium concentration of 0.5 mass ppm. 8.0 g (122 mmol) of lithium ethylmethylamide [LiN(CH$_3$)(CH$_2$CH$_3$)] was added into this flask, followed by agitation at room temperature for 1 hour. Subsequently, this reaction liquid underwent distillation under the condition of 100° C. and 0.12 kPa thereby obtaining 9.4 g of a fraction. The obtained fraction was tetrakis(ethylmethylamido)hafnium {Hf[N(CH$_3$)(CH$_2$CH$_3$)]$_4$} according to $^1$HNMR, and a zirconium concentration in the fraction was 0.8 mass ppm. A 2-phenyl-2-propanoxy lithium concentration in the fraction was not more than 100 mass ppm (yield: 82%).

Example 4

A 100 mL five-neck glass flask provided with a dropping funnel, a reflux condenser, a thermometer and an agitator was charged with 20.0 g (25.8 mmol) of the above-mentioned Compound No. 11 which was obtained by the synthesis of the above-mentioned (4) as a tertiary hafnium alkoxide complex and had a zirconium concentration of 0.4 mass ppm. 7.4 g (114 mmol) of lithium ethylmethylamide [LiN(CH$_3$)(CH$_2$CH$_3$)] was added into this flask, followed by agitation at room temperature for 1 hour. Subsequently, this reaction liquid underwent distillation under the condition of 100° C. and 0.12 kPa thereby obtaining 8.5 g of a fraction. The obtained fraction was tetrakis(ethylmethylamido)hafnium {Hf[N(CH$_3$)(CH$_2$CH$_3$)]$_4$} according to $^1$HNMR, and a zirconium concentration in the fraction was 0.8 mass ppm. A dimethyl benzyl carbinoxy lithium concentration in the fraction was not more than 100 mass ppm (yield: 80%).

Example 5

A 100 mL five-neck glass flask provided with a dropping funnel, a reflux condenser, a thermometer and an agitator was charged with 20.0 g (24.8 mmol) of the above-mentioned Compound No. 12 which was obtained by the synthesis of the above-mentioned (4) as a tertiary hafnium alkoxide complex and had a zirconium concentration of 0.4 mass ppm. 8.6 g (109 mmol) of lithium diethylamide [LiN(CH$_2$CH$_3$)$_2$] was added into this flask, followed by agitation at room temperature for 1 hour. Subsequently, this reaction liquid underwent distillation under the condition of 125° C. and 0.12 kPa thereby obtaining 9.0 g of a fraction. The obtained fraction was tetrakis(diethylamido)hafnium {Hf[N(CH$_2$CH$_3$)$_2$]$_4$} according to $^1$HNMR, and a zirconium concentration in the fraction was 0.7 mass ppm. A 3,7-dimethyl-3-octanoxy lithium concentration in the fraction was not more than 100 mass ppm (yield: 78%).

Example 6

A schematic illustration of a CVD apparatus used in this Example is shown in FIG. 1.

A raw material container 4 was charged with tetrakis(dimethylamido)hafnium {Hf[N(CH$_3$)$_2$]$_4$} produced according to the process of Example 1 and having a zirconium concentration of 0.9 mass ppm, as a raw material, in which argon gas 1 reduced in pressure by a pressure reducing valve 2a is introduced through a massflow controller 3a into the raw material container 4 so as to be used for liquid-feeding the charged raw material through a massflow controller 3b for liquid to a vaporizing chamber 5 and for purging the inside of the vaporizing chamber 5 before introduction of the raw material through a massflow controller 3c. The raw material introduced into the vaporizing chamber 5 was vaporized under heating and introduced into a reaction chamber 7. A vacuum pump 8 was connected to the reaction chamber 7 in order to reduce the pressure of the vaporizing chamber 5 and the reaction chamber 7. Argon gas 9 which was a gas for purging and used for removing unreacted raw material within the reaction chamber 7 was connected so as to be reduced in pressure by a pressure reducing valve 2b and introduced through a massflow controller 3d into the reaction chamber 7. Oxygen gas 10 was connected so as to be reduced in pressure by a pressure reducing valve 2c and introduced through a massflow controller 3e into an ozone generator 11 thereby introducing generated ozone as a reactive gas into the reaction chamber 7. The reaction chamber 7 was provided with a heating means capable of heating a Si substrate 6 located within the chamber, at a certain temperature.

After a hafnium-containing oxide film was formed on the Si substrate according to conditions and process discussed below using the CVD apparatus shown in FIG. 1, a zirconium concentration of the obtained hafnium-containing oxide film was measured by an ICP-MS apparatus (7500cs type, produced by Agilent Technologies).

[Conditions] Reactive gas: ozone, and reaction temperature (substrate temperature): 200° C.

[Process] After 80 cycles are repeatedly made in which one cycle includes a series of steps A→B→C→D mentioned below, an annealing treatment was carried out at a reaction temperature (substrate temperature) of 500° C.

A. Vapor of hafnium amide complex vaporized in the vaporizing chamber 5 in the conditions of a vaporizing chamber temperature of 150° C. and a vaporizing chamber pressure of 2 to 2.2 kPa was introduced into the reaction chamber 7 so that deposition was made for 2 seconds under a pressure of 2 to 2.2 kPa within a system.

B. Unreacted raw material was removed by argon purging for 3 seconds.

C. The reactive gas was introduced thereby making reaction for 2 seconds under a pressure of 1.3 kPa within the system.

D. Unreacted raw material was removed by argon purging for 3 seconds.

As a result, a zirconium concentration in the hafnium-containing oxide film was 1.5 mass ppm.

Example 7

Film Formation of Hafnium-Containing Oxide Film

Film formation of a hafnium-containing oxide film was accomplished by the same process as in the above-mentioned Example 6 except for using a raw material container charged with tetrakis(ethylmethylamido)hafnium {Hf[N(CH$_3$)(CH$_2$CH$_3$)]$_4$} produced according to the process of Example 3 and having a zirconium concentration of 0.8 mass ppm. A zirconium concentration of the obtained hafnium-containing oxide film was measured by the ICP-MS apparatus. As a result, the zirconium concentration in the hafnium-containing oxide film was 1.6 mass ppm.

Comparative Example 1

The same process as in Example 2 was carried out except for using 11.2 g (31.3 mmol) of tetraethoxy hafnium [Hf(OCH$_2$CH$_3$)$_4$] which was a primary hafnium alkoxide complex and had a zirconium concentration of 0.9 mass ppm, in place of the above-mentioned Compound No. 3 as a tertiary hafnium alkoxide complex; however, no distillate could be obtained.

Comparative Example 2

The same process as in Example 2 was carried out except for using 12.9 g (31.3 mmol) of tetraisopropoxy hafnium {Hf[OCH(CH$_3$)$_2$]$_4$} which was a secondary hafnium alkoxide complex and had a zirconium concentration of 0.8 mass ppm, in place of the above-mentioned Compound No. 3 as a tertiary hafnium alkoxide complex; however, no distillate could be obtained.

Comparative Example 3

Production of tetrakis(ethylmethylamido)hafnium was made by the same process as in Example 2 except for using 14.7 g (31.3 mmol) of tetra-tertiary-butoxy hafnium {Hf[O(CH$_3$)$_3$]$_4$} which was a primary hafnium alkoxide complex and had a zirconium concentration of 0.7 mass ppm, in place of the above-mentioned Compound No. 3 as a tertiary hafnium alkoxide complex, thereby obtaining 12.3 g of a fraction. The obtained fraction was a mixture of tetrakis(ethylmethylamido)hafnium and tertiary-butoxy lithium according to $^1$HNMR. A tertiary-butoxy lithium concentration in the fraction was 21 mass %.

Comparative Example 4

Production of tetrakis(ethylmethylamido)hafnium was made by the same process as in Example 2 except for using 16.5 g (31.3 mmol) of tetra(2-methyl-2-butoxy)hafnium {Hf[OC(CH$_3$)$_2$(CH$_2$CH$_3$]$_4$} which was a tertiary hafnium alkoxide complex and had a zirconium concentration of 0.7 mass ppm, in place of the above-mentioned Compound No. 3 as a tertiary hafnium alkoxide complex, thereby obtaining 11.6 g of a fraction. The obtained fraction was a mixture of tetrakis(ethylmethylamido)hafnium and 2-methyl-2-butoxy lithium according to $^1$HNMR. A 2-methyl-2-butoxy lithium concentration in the fraction was 12 mass %.

Comparative Example 5

A 3 L five-neck glass flask was provided with a reflux condenser, a thermometer, a dropping funnel and an agitator, and nitrogen substitution was made for the inside of the flask. This flask was charged with 160 g of hafnium tetrachloride (HfCl$_4$) having a zirconium concentration of 950 mass ppm and 0.4 L of hexane. After a reaction pot was ice-cooled, a lithium ethylmethylamide [LiN(CH$_3$)(CH$_2$CH$_3$)] solution which had been separately prepared from n-butyl lithium and ethylmethyl amine was dropped from the dropping funnel over 3 hours. Further, after agitation was made at an ice-cooled temperature for 1 hour, a reduced-pressure distillation was carried out at 110° C. and at 0.12 kPa thereby obtaining 143 g of a fraction. The obtained fraction was tetrakis(ethylmethylamido)hafnium {Hf[N(CH$_3$)(CH$_2$CH$_3$)]$_4$} according to $^1$HNMR, and a zirconium concentration in the fraction was 840 mass ppm (yield=75%).

Production of a hafnium-containing oxide film was accomplished by the same process as in Example 6 except for using the obtained tetrakis(ethylmethylamido)hafnium {Hf[N(CH$_3$)(CH$_2$CH$_3$]$_4$} having a zirconium concentration of 840 mass ppm. A zirconium concentration of the obtained hafnium-containing oxide film was measured by the ICP-MS apparatus. As a result, the zirconium concentration in the hafnium-containing oxide film was 1640 mass ppm.

EXPLANATION OF REFERENCE 1, 9: argon gas
2a, 2b, 2c: pressure reducing valve
3a, 3c, 3d, 3e: massflow controller
3b: massflow controller for liquid
4: raw material container
5: vaporizing chamber
6: Si substrate
7: reaction chamber
8: vacuum pump
10: oxygen gas
11: ozone generator

The invention claimed is:

1. A method of producing a hafnium amide complex represented by a general formula: Hf(NR$_4$R$_5$)$_4$, comprising:
   carrying out a reduced-pressure distillation after a lithium alkylamide represented by a general formula: Li(NR$_4$R$_5$) is added to and allowed to react with a tertiary hafnium alkoxide complex represented by a general formula: Hf[O(CR$_1$R$_2$R$_3$)]$_4$, wherein
   R$_1$, R$_2$ and R$_3$ independently represent either a phenyl group, a benzyl group, or a primary, secondary or tertiary alkyl group having a carbon number 1-6; and
   R$_4$ and R$_5$ independently represent either a methyl group or an ethyl group; excluding all of R$_1$, R$_2$ and R$_3$ being methyl groups, and excluding one of R$_1$, R$_2$ and R$_3$ being an ethyl group and the other two being methyl groups.

* * * * *